United States Patent [19]

Kiser et al.

[11] Patent Number: 5,327,909
[45] Date of Patent: Jul. 12, 1994

[54] EPICARDIAL DEFIBRILLATOR LEAD

[75] Inventors: Joseph C. Kiser, Excelsior; James D. Madison, White Bear Lake, both of Minn.

[73] Assignee: Angeion Corporation, Plymouth, Minn.

[21] Appl. No.: 691,987

[22] Filed: Apr. 26, 1991

[51] Int. Cl.$^5$ ............................................... A61N 1/05
[52] U.S. Cl. ...................................................... 607/129
[58] Field of Search ........................ 128/642, 784, 785

[56] References Cited

U.S. PATENT DOCUMENTS

| | | | |
|---|---|---|---|
| 4,765,341 | 8/1988 | Mower et al. | 128/785 |
| 4,827,932 | 5/1989 | Ideker et al. | 128/642 |
| 5,042,463 | 8/1991 | Lekholm | 128/642 |

OTHER PUBLICATIONS

McCowan, et al., "Automatic Implantable Cardioverter-Defibrillator Implantation Without Thoractomy Using an Endocardial and Submuscular Patch System", JACC, vol. 17, No. 2, Feb. 1991.

Smith et al., "Right Atrial Perforation by a Temporary Epicardial Pacing Wire", Ann. Thorac. Surg, 1990, vol. 50, pp. 141-142.

Crozier et al., "Automatic Implantable Defibrillators", British Journal of Hospital Medicine, vol. 40, Aug. 1988, pp. 136-139.

Lerman, et al., "Relation Between Transcardiac and Transthoracic Current During Defibrillation inHumans", Circulation Research, vol. 67, No. 6, Dec. 1990, pp. 1420-1426.

Grubb et al., "Technique for Intraoperative Arrhythmia Induction During Automatic Implantable Defibrillator Placement", PACE, vol. 13, Aug. 1990, pp. 958-960.

Korompai, et al., "Migration ot Temporary Epicardial Pacer Wire Fragment Retain-d after a Cardiac Operation", Journal of Thoracic and Cardioversion Surgery, vol. 94, No. 3, Sep. 1987, pp. 446-447.

*Primary Examiner*—William E. Kamm
*Assistant Examiner*—Scott M. Getzow
*Attorney, Agent, or Firm*—Patterson & Keough

[57] ABSTRACT

An epicardial defibrillator lead which is placed into a paracardial space adjacent the phrenic nerve and is supported in position by the paracardium wall. A soft-nosed, rounded, blunt-nosed introducer provides for positioning of the defibrillator lead in the paracardial space. The electrode is formed on one side of a polymer member, which is conforming to the left ventricle and the paracardium wall. The electrode has a polymer backing to insulate the electrode from the paracardium wall. The electrode of the defibrillator lead conforms to the geometrical shape of the left ventricle.

2 Claims, 6 Drawing Sheets

EPICARDIAL DEFIBRILLATOR LEAD

BACKGROUND OF THE INVENTION

1. Field of the Invention

The present invention pertains to an epicardial defibrillator lead for the heart, and more particularly, pertains to an epicardial defibrillator lead which is positioned through a small incision or percutaneously in the paracardial space.

2. Description of the Prior Art

Prior art defibrillator leads have required major surgery for the patient, and the mortality rates for such patients is excessive. The surgical procedure for the prior art defibrillator leads required opening of the thoracic cavity, opening of the paracardial sac, and placing the electrode of the defibrillator lead in contact with the left ventricle.

The present invention overcomes the disadvantages of the prior art procedures for the prior art defibrillator leads by providing an epicardial defibrillator lead which can be inserted through a small incision or percutaneously in the paracardial space. The defibrillator lead positions between the left ventricle and the paracardial wall.

SUMMARY OF THE INVENTION

The general purpose of the present invention is an epicardial defibrillator lead for positioning between the left ventricle and the paracardial wall through a small incision or percutaneously in the paracardial space. The epicardial defibrillator lead can be positioned through a soft-nosed, rounded, blunt tip introducer.

According to one embodiment of the present invention, there is provided an epicardial defibrillator lead which can be passed through a soft-nosed, rounded, blunt tip electrode introducer. The electrode is positioned on a polymer member which rests against the paracardial space when positioned in the paracardial space adjacent the phrenic nerve.

Significant aspects and features of the present invention include an epicardial defibrillator lead which can be inserted percutaneously or through a small incision in the paracardial wall.

Another object of the present invention is an epicardial defibrillator lead which can be positioned between the left ventricle and in the paracardial space, and more importantly, positions adjacent to the phrenic nerve.

Having thus described embodiments of the present invention, it is a principal object hereof to provide an epicardial defibrillator lead.

One object of the present invention is to provide an epicardial defibrillator lead which can be inserted through a small incision or percutaneously in the paracardial sac.

Another object of the present invention is an epicardial defibrillator lead which is flexible and conforming to the geometrical shapes of the left ventricle and the paracardial sac.

A further significant aspect and feature of the present invention is an epicardial defibrillator lead which can be inflated to position the defibrillator lead prior to tissue ingrowth about the defibrillator lead for holding the electrode in place.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

FIG. i illustrates a front perspective view of an epicardial defibrillator lead, the present invention.

DESCRIPTION OF THE PREFERRED EMBODIMENTS

Figure 1:
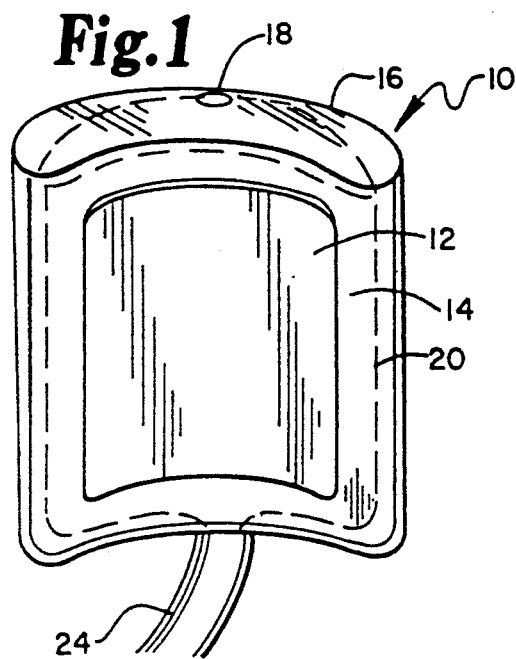

FIG. 1 illustrates a perspective view of an epicardial defibrillator lead 10 including an electrode surface 12 on a front polymer surface 14, which is geometrically conforming to the left ventricle of the heart. A polymer back surface 16, such as silastic-like material, which is also geometrically conforming to the paracardial wall, affixes about the edges of the front polymer surface 12. An optional hole 18 can be provided between the surfaces for optionally passing the defibrillator lead 10 up a guide wire, and between the left ventricle and the paracardial wall to be adjacent to the phrenic nerve. An internal inflation balloon member 20 positions between the polymer front surface 14 and polymer back surface 16 and connects to an inflation lumen 22. An electrode wire 24 connects to the electrode 12. The electrode wire 24 and the inflation lumen 22 position in a longitudinal jacket 26 which connects to the base of the defibrillator lead 10. The entire structure of members 12-20 can be rolled or spiraled about themselves for passage through a hollow, soft-tipped, blunt-nosed catheter.

Figure 2:
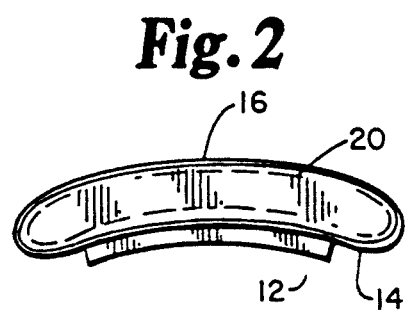
FIG. 2 illustrates a top view of the present invention.

FIG. 2 illustrates a top view of the present invention where all numerals correspond to those elements previously described.

Figure 3:
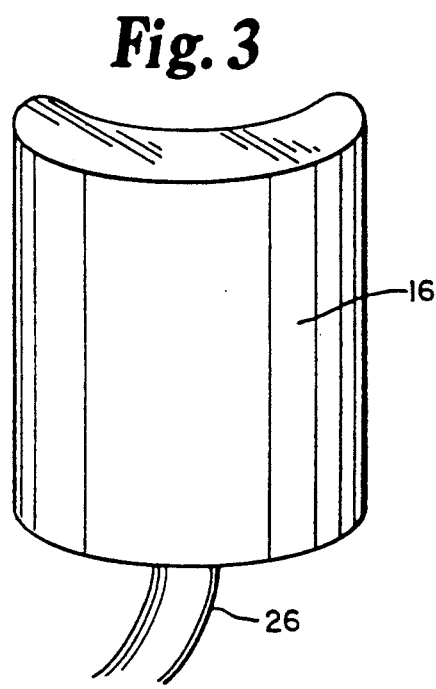
FIG. 3 illustrates a back view of the present invention.

FIG. 3 illustrates a back view of the present invention where all numerals correspond to those elements previously described.

Figure 4:
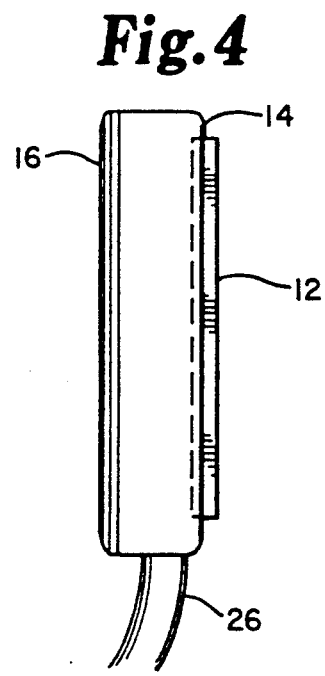
FIG. 4 illustrates a side view of the present invention.

FIG. 4 illustrate a side view of the present invention where all numerals correspond to those elements previously described.

MODE OF OPERATION

Figure 5:
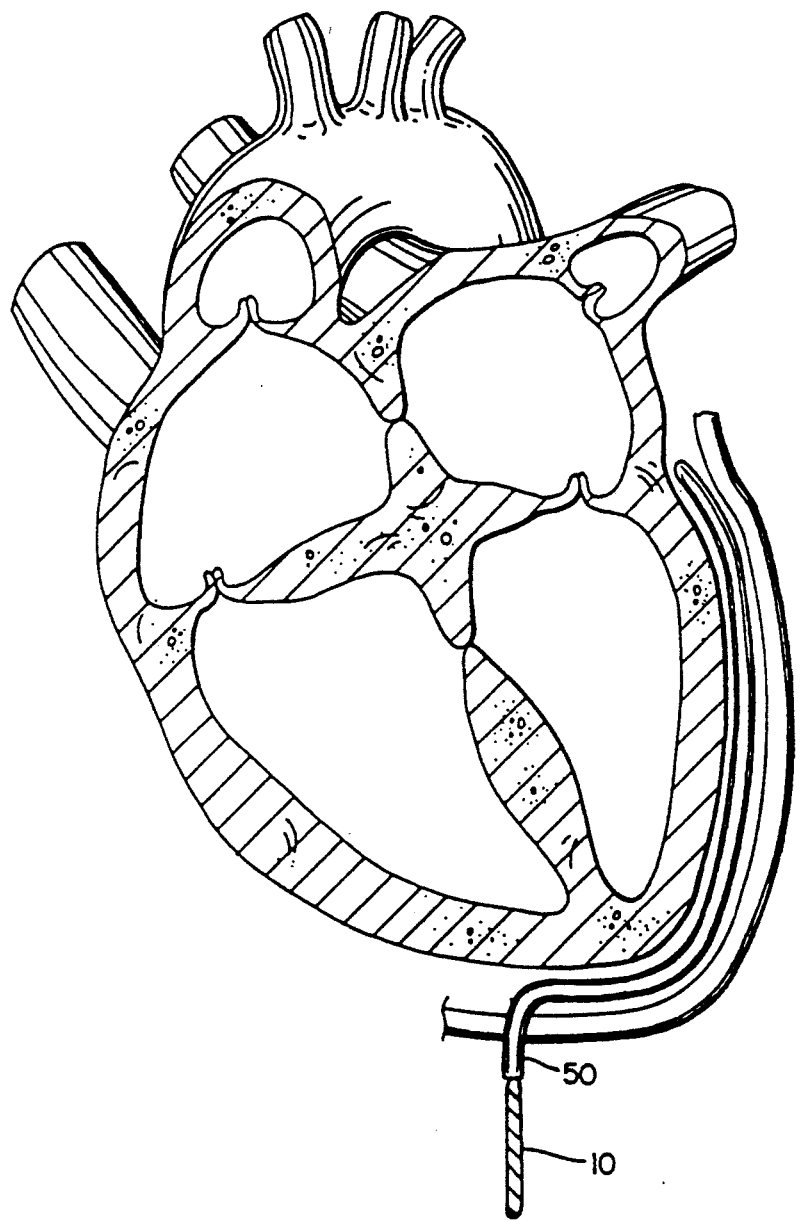
FIGS. 5-8 illustrate the mode of operation of the present invention.
Figure 6:
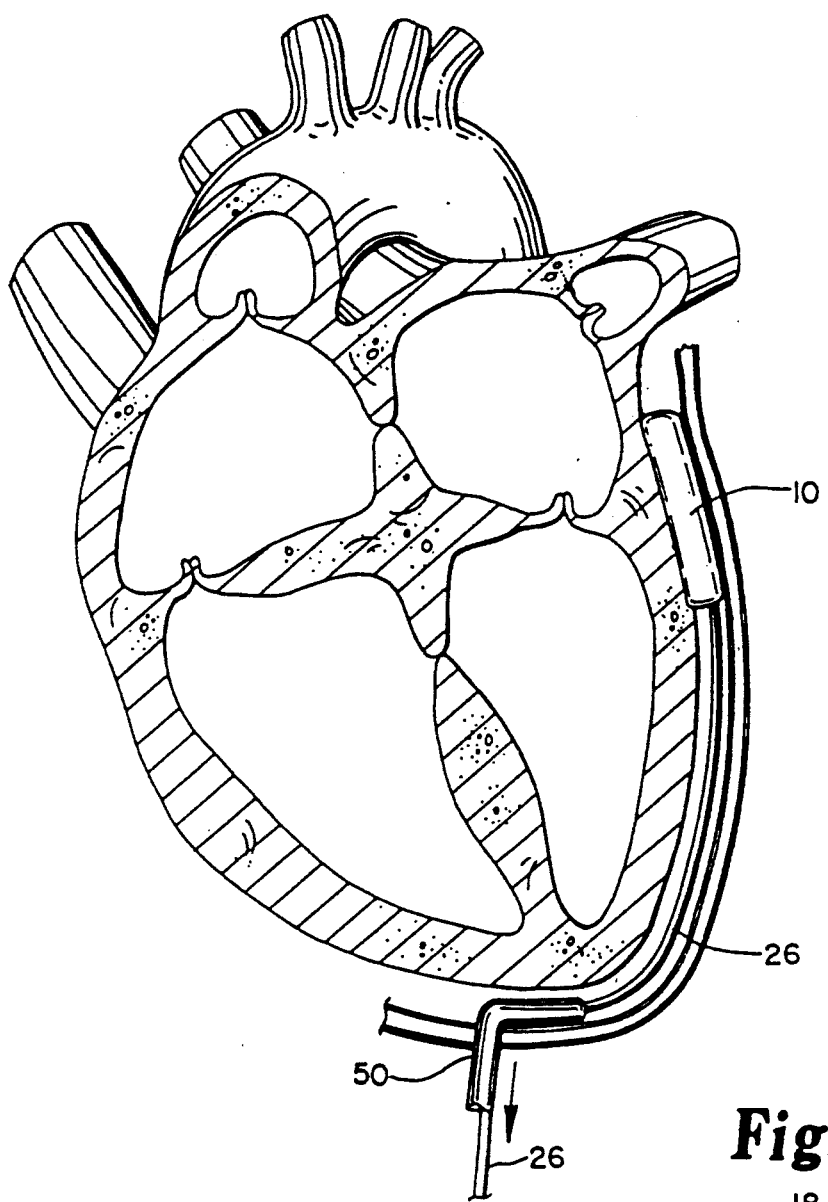
Figure 13:
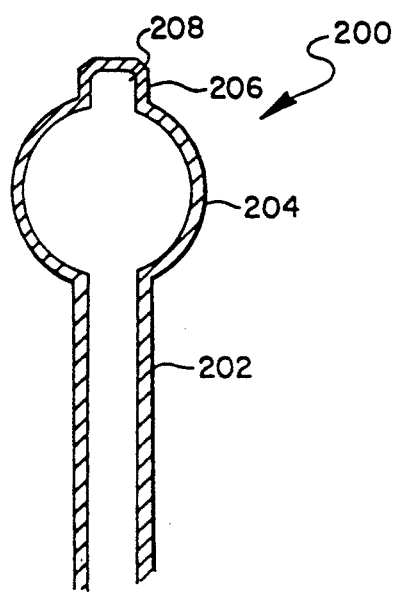
FIG. 13 illustrates a cross-sectional view of a blunt-nosed soft tip introducer for the present invention; and, FIG. 14 illustrates an alternative embodiment of an epicardial defibrillator lead.

As illustrated in FIG. 5, the defibrillator lead 10 can be rolled or furled, such as spirally rolled, for passage through a hollow, soft-tipped, blunt-nosed catheter 50 with a rounded bolus and having a very thin tip. A rounded, soft-tipped, blunt-nosed catheter, as illustrated in FIG. 13, is used for passage of the defibrillator lead 10 prior to inflation or positioning in the paracardial space. The rounded bolus of the soft-tipped, blunt-nosed catheter is positioned over a guide wire, which as been previously inserted through a small incision or percutaneously in the lower paracardial wall, and then passed between the paracardial space of the left ventricle and the paracardial wall adjacent to the phrenic nerve. Next, the defibrillator lead 10 is passed up through the soft-tipped, blunt-nosed catheter 50, and then the soft-tipped, blunt-nosed catheter 50 is removed as in FIG. 6. The defibrillator lead 10 can then be partially inflated to flatten the defibrillator lead.

Figure 8:
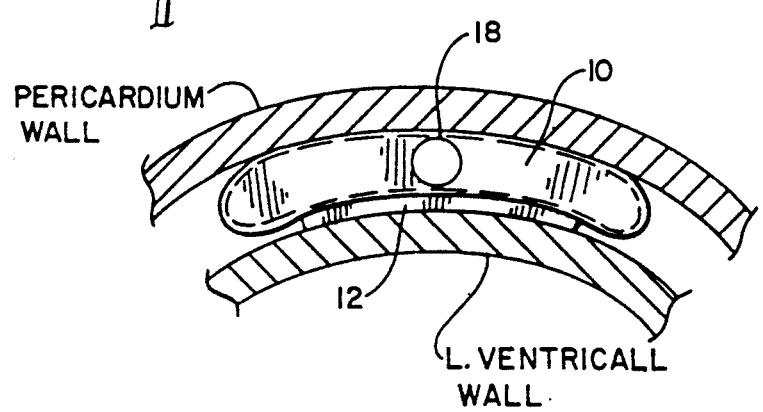
Figure 7:
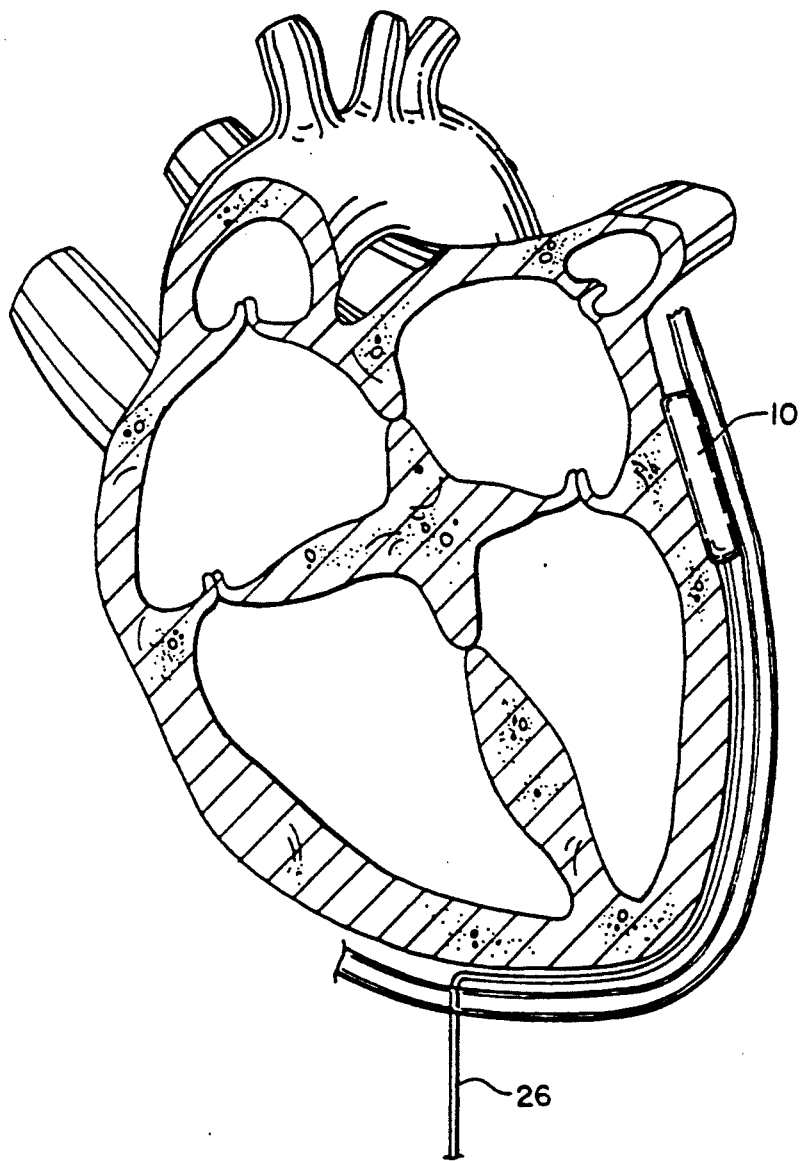
Figure 9:
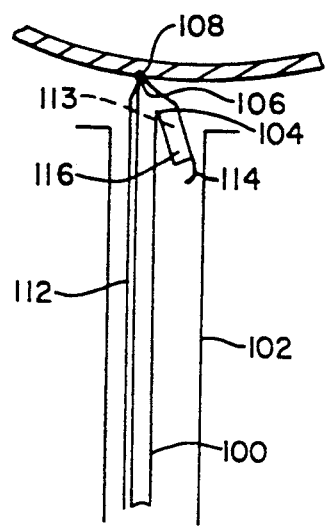
FIGS. 9-12 illustrate a guide wire introducer for the present invention.
Figure 10:
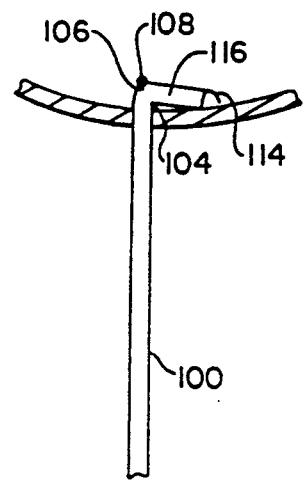
Figure 11:
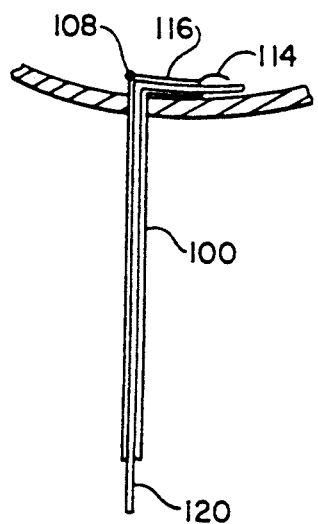

Under a fluoroscopy procedure, the electrode 12 is aligned adjacent to the phrenic nerve in the left ventricle wall. The defibrillator lead 10 can be inflated with a water or saline solution as in FIG. 7, and eventually, tissue growth may affix the defibrillator lead in the event the inflated defibrillator lead were to deflate, such as because of the natural tendencies of the materials, etc. The tissue ingrowth can affix the defibrillator lead in position. FIG. 8 illustrates a cross-sectional view of the defibrillator lead with the electrode in place.

Figure 12:
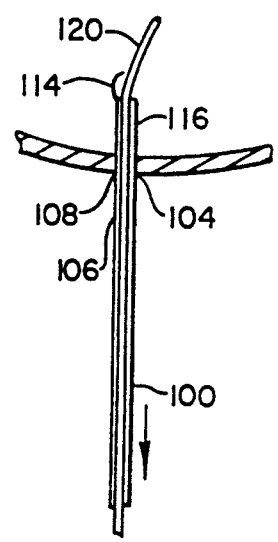

FIGS. 9-12 illustrate operational plan views of a guide wire introducer 100 for the paracardial sac. It is very important when introducing the guide wire that the guide wire be properly aligned in the paracardial space and properly moved about the left ventricle. In the event that the guide wire were improperly positioned, then the guide wire could possibly puncture the right ventricle, which would be less than desirable. The guide wire introducer is a disposable, tubular type member 100 with an insert sleeve 102. The guide wire introducer 100 includes living hinges 104 and 106 for tip movement as later described in detail. An EKG electrode 108 positions above the sharp living hinge 106 and attaches to a thin, insulated wire 112 molded into the guide wire introducer 100 for later connection to an EKG system. The EKG electrode provides for sensing of the position of the guide wire introducer about the heart, such as at the right ventricle. The guide wire introducer includes a hollow lumen 113 for passage of a guide wire and a semicircular end 114 to provide for the guided passage of the guide wire introducer 100 about the paracardial space and about the left ventricle. The living hinge structures 104 and 106 provide for the bending of the upper most end 116 of the guide wire introducer so that the introducer can puncture the paracardial wall as in FIG. 9 by the sharp hinge edge 106, and can be appropriately maneuvered for passage of the guide wire as in FIG. 10 and especially FIG. 11. The guide wire introducer 100 is then removed after there is placement of the guide wire 120 as illustrated in FIG. 12 so that a soft-tipped, blunt-nosed catheter can then be inserted over the guide wire and guided up the paracardial space to about the left ventricle. The guide wire introducer 100 can be made of a suitable polymer and coated with an appropriate radiopaque material for observation under a fluoroscope. The introducer sleeve 102 can also be provided with a radiopaque material for observation under a fluoroscope. The substance of the present invention of the guide wire introducer 100 is to provide a path for the guide wire up through the paracardial space by the left ventricle.

A soft tipped, blunt-nosed catheter with a thin wall is passed over the guide wire prior to removal of the guide wire, and provides for passage of the defibrillator lead 10 with the inflatable electrode structure.

FIG. 13 illustrates a view in cross section of a soft-tipped, blunt-nosed catheter. The soft-tipped, blunt-nosed catheter 200 includes a flexible lower member 202, a bolus type bulb 204, and a thin, soft-tipped edge 206 with a slightly inwardly projecting lip 208. The edge 206 and the lip 208 are thin walled so as not to rake the left ventricle or the paracardial wall. The longitudinal lower portion 202 is of a material to be flexible to bend about the guide wire and conform to the paracardial space. The catheter can also be provided with a radiopaque coating or radiopaque threads of material for visibility under a fluoroscope.

DESCRIPTION OF THE ALTERNATIVE EMBODIMENT

Alternatively, the electrode and lead can be surgically inserted and positioned under direct vision. A local anesthetic is introduced in the subxiphoid area. A small cut-down then exposes the paracardium. The parietal is then exposed through a small pericardiotomy, an incision forming a hole in the paracardium. The electrode is then positioned adjacent the left ventricle at a preferred location. The preferred location is determined by sensing potentials. The electrode is unwrapped or unfurled, such as by inflating the electrode with water or a saline solution. The electrode then unwraps or unfurls and locates itself in position.

In an alternative embodiment, an electrode surface can be positioned on each side of the polymer surface so that the lead can be rotated in either direction to position an electrode surface against the left ventricle.

Figure 14:
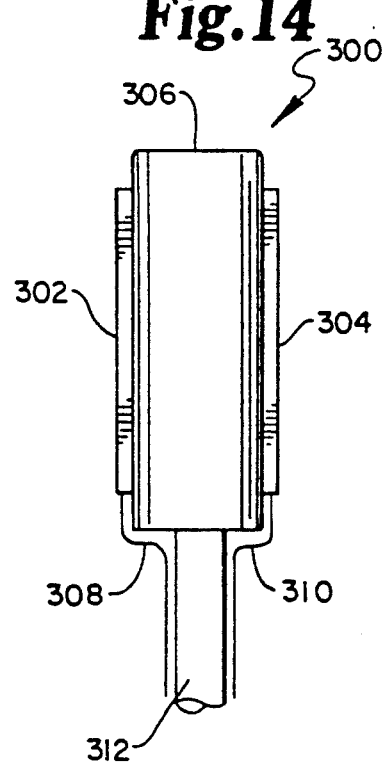

FIG. 14 illustrates a side view of an electrode defibrillator lead 300 with two electrode surfaces 302 and 304 positioned on opposing surfaces of an unwrapped or unfurled polymer member 306 similar to a flat rectangular inflatable member. Two separate conducting members 308 and 310 connect to each of the electrodes 302 and 304. A tube 312 attaches to the polymer member for unwrapping or unfurling of the polymer member by pressurized liquid such as a water solution or a saline solution.

Various modifications can be made to the present invention without departing from the apparent scope hereof:

I claim:

1. A cardiac defibrillator lead for insertion through a small incision or percutaneous in the pericardial wall of a heart comprising:
   a. a first insulating member outer surface;
   b. a second insulating member outer surface spaced apart from said first insulating member outer surface and including a defibrillator electrode on said second insulating member outer surface;
   c. an electrical lead connected to said electrode; and,
   d. inflation means between said insulating member outer surfaces for extending said outer surfaces outward after insertion of said cardiac defibrillator lead.

2. The cardiac defibrillator lead of claim 1 wherein said defibrillator electrode is adapted for placement adjacent to a phrenic nerve in the left ventricle of said heart.

* * * * *